United States Patent [19]

Golub

[11] 4,297,995
[45] Nov. 3, 1981

[54] BANDAGE CONTAINING ATTACHMENT POST

[75] Inventor: Allyn L. Golub, Coral Gables, Fla.

[73] Assignee: Key Pharmaceuticals, Inc., Miami, Fla.

[21] Appl. No.: 156,025

[22] Filed: Jun. 3, 1980

[51] Int. Cl.³ .............................................. A61L 15/00
[52] U.S. Cl. .................................... 128/156; 128/260
[58] Field of Search .............. 128/155, 156, 268, 260, 128/390

[56] References Cited

U.S. PATENT DOCUMENTS 2,489,675  11/1949  Roberts .............................. 128/156
3,416,525  12/1968  Yeremian .......................... 128/156
3,491,753   1/1970  Milton et al. ...................... 128/156

Primary Examiner—John D. Yasko
Attorney, Agent, or Firm—Wegner & Bretschneider

[57] ABSTRACT

A bandage is disclosed comprising a lower portion and a matrix. The lower portion has an upper surface, a base plate on the upper surface, and a post extending from the surface of the base plate. The matrix is attached to the lower portion by means of a hole extending through the matrix which fits around the post. The upper surface of the lower portion can be adhesively coated if desired. The lower portion can also be in the form of a strap. The base plate can be composed of a suitable barrier material such as metal foil or metal foil - polyester laminates. If desired, the matrix can be of a material which can dispense medicaments such as trinitroglycerol.

22 Claims, 9 Drawing Figures

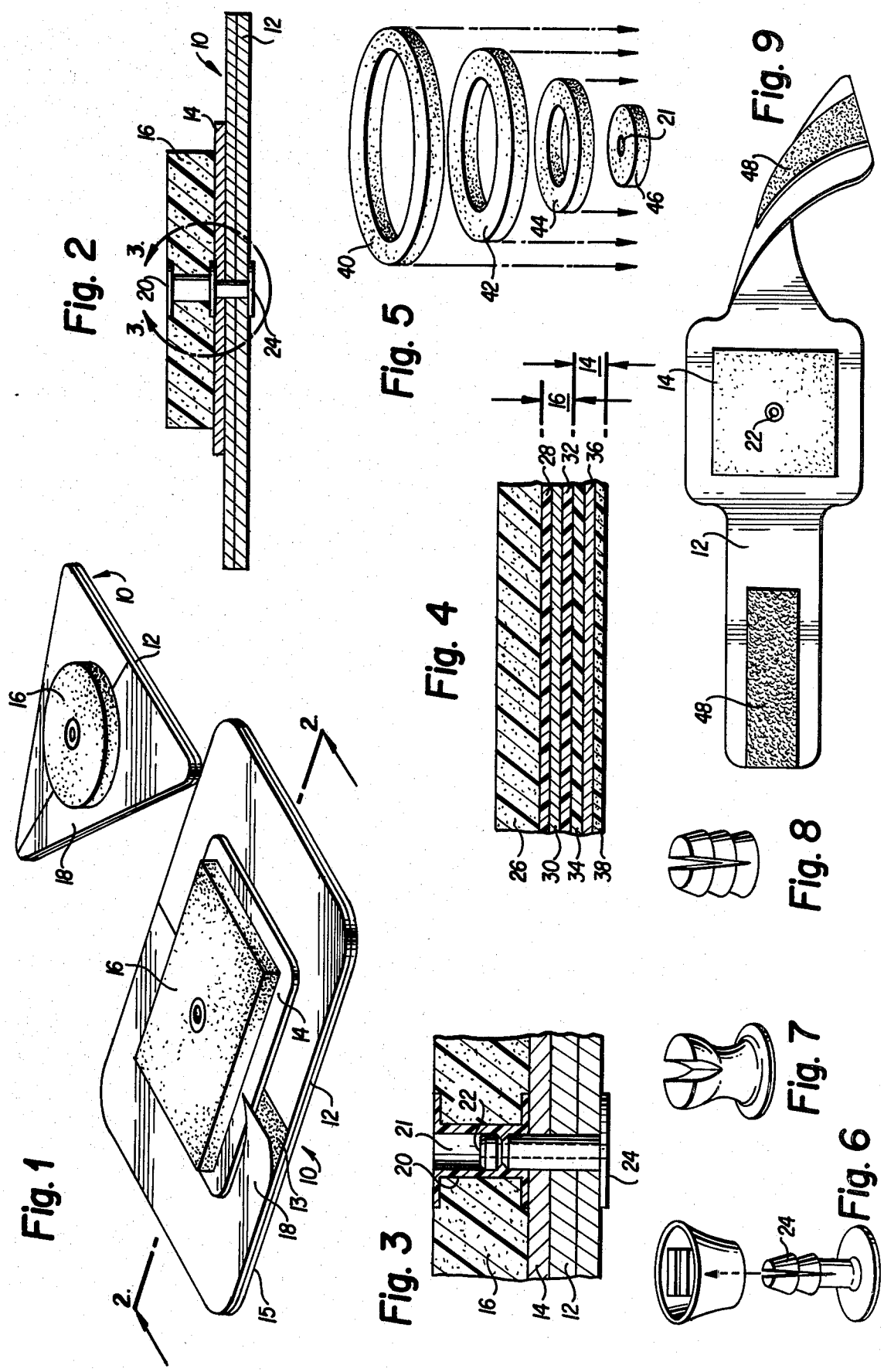

BANDAGE CONTAINING ATTACHMENT POST

BACKGROUND OF THE INVENTION

1. Field of the Invention

This invention relates to bandages, and more particularly, to a bandage which can be assembled just prior to use and which can dispense a medicament if desired.

2. Description of the Prior Art

Bandages are in general of course well known in the art. However, bandages in the past have been of basically unitary construction and have been intended more for protective rather than therapeutic uses.

SUMMARY OF THE INVENTION

It is an object of this invention to provide a bandage of simple construction.

It is a further object of this invention to provide a bandage which can be used for administering therapeutic doses of a medicament.

It is a still further object to provide a bandage which can be assembled by the patient prior to use.

It is a still further object to provide a bandage which is easily and economically fabricated.

The above objects and others are obtained by providing a bandage composed of readily assembled pieces. The first piece is made up of a lower portion, a base plate attached to the lower portion, and a post extending from the surface of the base plate. The second piece of the bandage is a matrix, which is attached to the first piece by means of a hole in the matrix which fits around the post of the first piece. For the purposes of this invention, a matrix is defined as a material that will contact the skin of a patient for healing or other therapeutic purposes. Thus a matrix is intended to refer to both a conventional bandage pad and an assembly that contains a medicament.

To facilitate attachment of the bandage to a patient, the lower portion can be adhesively coated. In another embodiment, the lower portion can be in the form of a strap having suitable fastening means at its ends. The base plate can be composed of any suitable barrier material, some examples of which are metal foil of "polyfoil" (a laminate of plastic and a metal foil). The matrix can be composed of a material containing a therapeutic dosage of a medicament and which allows sustained release of the medicament.

BRIEF DESCRIPTION OF THE DRAWINGS

FIG. 1 is a perspective view of two bandages of the present invention having different shapes and sizes;

FIG. 2 is a sectional side view of the bandage taken along line 2—2 of FIG. 1;

FIG. 3 is an enlarged sectional side view of the bandage taken along line 3—3 of FIG. 2, showing the assembly of the bandage in detail;

FIG. 4 is a sectional side view of another embodiment of the base plate and matrix;

FIG. 5 is a perspective view of another configuration of the matrix;

FIGS. 6 through 8 show alternative constructions of the post; and

FIG. 9 is a top view of an alternative embodiment of the bandage wherein the lower portion is in the form of a strap.

DESCRIPTION OF THE PREFERRED EMBODIMENT

Referring to FIGS. 1 through 3, the bandage 10 is generally composed of a lower portion 12, a base plate 14 from which post 22 extends, and matrix 16. The matrix 16 is secured to the rest of the bandage by means of hole 21 which extends through the matrix and fits around post 22. The hole 21 can be, but is not necessarily, defined by eyelet 20. The post can be attached to the base plate by means of a rivet 24 extending through the lower portion and base plate as shown in FIG. 3. The rivet can also extend through the base plate alone (not shown). Other forms of attachment, such as adhesive attachment, are also readily useable as a means for attachment.

The lower portion 12 is composed of a backing (or first) layer 15 and an adhesive layer 13 applied to the upper surface of the backing layer. A release liner 18 may be utilized to prevent unwanted adhesion prior to use.

The base plate 14 can be composed of any suitable barrier material, such as metal foil or metal foil-polymer laminates ("polyfoils"). Other possible base plate combinations include, but are not limited to, aluminum foil-polyester, Surlyn-polypropylene, polyamide-aluminum foil-polyvinyl chloride ("Alusuisse"), polyethylene-polyester, and bilaminate foil CX-220 manufactured by the Ludlow Packaging division of Ludlow Corporation, Holyoke, Mass. 01040. In the preferred embodiment shown in FIG. 4, the base plate is composed of a polyethylene layer 34, an aluminum foil layer 36, and a polyester layer 38. The "Alusuisse" embodiment specifically consists of an 18 micron thick layer of polyamide, a 40 micron thick layer of aluminum foil, and a 60 micron thick layer of polyvinylchloride.

The matrix 16 can be composed of any suitable bandage material such as a cotton batt or a synthetic bandage material, e.g. a polyester like polyethylene terephthalate. The matrix can also have several layers such as an aluminum foil layer and a polyester layer, or as shown in FIG. 4, a layer of polyethylene 32, an aluminum foil layer 30, a layer of polyethylene 28, and a polyester layer 26.

The matrix can also be further composed of a medicament containing-dispensing layer. An example of this type of matrix is disclosed in U.S. pat application Ser. 109,242 to Keith et al, entitled "Polymeric Diffusion Matrix", filed Jan. 3, 1980, incorporated by reference herewith. That application discloses a polymeric diffusion matrix composed of glycerol, a polyvinyl alcohol, and a water soluble polymer with hydration sites, e.g. polyvinyl pyrrolidone. This matrix provides sustained release of a medicament which is introduced to the matrix during manufacture of the matrix. An example of a medicament which can be dispensed from such a matrix is trinitroglycerol, which is used as a vasodilator for treating heart conditions.

The hole 21 should be of such a size as to fit snugly around the post 22, the post 22 preferably being constructed so that at some point, the body of the post is wider than at a point immediately closer the base of the post. This structure provides a more secure holding of the matrix. The length of the post should also be less than the thickness of the matrix to prevent possible injury to the patient.

FIG. 5 shows a matrix of a variable size, wherein the size of the matrix can be increased by adding concentric rings 40, 42 and 44 to central matrix 46 containing hole 21, or decreased by removing concentric rings 40, 42, and 44.

FIGS. 6, 7 and 8 show various configurations for the post. FIG. 6 also shows a configuration for rivet 24. If a hollow post and rivet are provided, the post attachment bandage can be used as an I.V. tube supporter, with the I.V. tube extending through the rivet and post and then into the patient.

FIG. 9 shows a second embodiment for the bandage. In this embodiment, the lower portion 12 is in the form of a strap. The bandage is shown without the matrix attached. The strap is provided with fasteners 48 on each end of the strap. One suitable fastener is a flexible fabric fastener of an interconnectible series of loops and hooks, the fastener being located on opposite faces of the strap. This fastener is commonly known as a "Velcro" fastener in the trade. Other suitable fasteners such as snaps or adhesives are also readily conceived.

The bandage can be packaged by having the combination of the lower portion, baseplate and post enclosed in one package and the matrix in another package. When the patient desires to use the bandage, he can open the two packages and attach the matrix to the post. This is advantageous if different types of packaging are desirable for the matrix and lower portion.

What is claimed is:

1. A bandage comprising:
   (a) a lower portion comprising
      (1) a first layer having an upper surface;
      (2) a base plate having an upper face and a lower face, said lower face being attached to said upper surface of said first layer, said base plate having a surface area less than the surface of said upper surface of said first layer;
   (b) a post extending upwardly from the upper face of said base plate; and
   (c) a matrix having an upper surface and a lower surface and a hole extending from said lower surface to said upper surface, said lower surface being in intimate contact with the upper face of said base plate, said post passing through said hole.

2. A bandage comprising:
   (a) a lower portion comprising:
      (1) a first layer having an adhesively coated upper surface; and
      (2) a base plate having an upper face and a lower face, said lower face being attached to said adhesively coated upper surface of said first layer, said base plate having a surface area less than the surface area of said adhesively coated upper surface of the first layer;
   (b) a post extending upwardly from the upper face of said base plate; and
   (c) a matrix having an upper surface and a lower surface and a hole extending from said lower surface to said upper surface, said lower surface being in intimate contact with the upper face of said base plate, said post passing through said hole.

3. The bandage of claim 1 or 2 wherein said base plate is a metal foil.

4. The bandage of claim 2 further comprising a release liner in contact with the adhesively coated upper surface of said first layer.

5. The bandage of claim 1 or 2 wherein said matrix has a surface area less than the surface area of said base plate.

6. The bandage of claim 4 wherein said release liner surrounds said base plate.

7. The bandage of claim 3 wherein said metal foil is a laminate containing aluminum foil and a polyester layer.

8. The bandage of claim 1 or 2 wherein in said post is adhesively attached to said base plate.

9. The bandage of claim 1 or 2 wherein said post is attached to said base plate by a rivet extending through said base plate and said first layer.

10. The bandage of claim 1 or 2 wherein said post is attached to said base plate by a rivet extending through said base plate.

11. The bandage of claim 1 or 2 wherein the hole in said matrix is defined by an eyelet.

12. The matrix of claim 1 or 2 wherein said matrix contains a medicament.

13. The bandage of claim 1 or 2 wherein said matrix comprises a series of concentric matrices having a central matrix.

14. The bandage of claim 13 wherein said hole is located in said central matrix.

15. The bandage of claim 1 wherein the first layer of said lower portion is a strap.

16. The bandage of claim 15 wherein said strap comprises opposite faces each having a flexible fabric fastener of an interconnectable series of loops and hooks.

17. The bandage of claim 1 or 2 wherein said matrix includes a laminate containing aluminum foil and a polyester.

18. The bandage of claim 17 wherein said matrix comprises a layer of polyethylene, a layer of aluminum foil, a thin layer of polyethylene, and a layer of polyester.

19. The bandage of claim 18 wherein said matrix further comprises a layer containing a medicament.

20. The bandage of claim 19 wherein said medicament is trinitroglycerol.

21. The bandage of claim 1 or 2 wherein said post has a bottom next to said base plate, at some point said post having a greater cross sectional area than the cross sectional area at a point immediately closer to said bottom.

22. The bandage of claim 1 or 2 wherein said post has a length shorter than the thickness of said matrix.

* * * * *